(12) United States Patent
Patel et al.

(10) Patent No.: US 11,759,287 B2
(45) Date of Patent: Sep. 19, 2023

(54) METHOD FOR CLEANING AND LUBRICATING AN ANGIOGRAPHIC WIRE WITH FLUID SOLVENT DELIVERY

(71) Applicants: Dhruv Patel, Saint Cloud, FL (US); Anthony Cascio, Land O' Lakes, FL (US)

(72) Inventors: Dhruv Patel, Saint Cloud, FL (US); Anthony Cascio, Land O' Lakes, FL (US)

(*) Notice: Subject to any disclaimer, the term of this patent is extended or adjusted under 35 U.S.C. 154(b) by 355 days.

(21) Appl. No.: 17/206,428

(22) Filed: Mar. 19, 2021

(65) Prior Publication Data

US 2021/0205045 A1 Jul. 8, 2021

Related U.S. Application Data

(62) Division of application No. 16/016,202, filed on Jun. 22, 2018, now Pat. No. 10,987,194.

(51) Int. Cl.

| | | |
|---|---|---|
| *B05D 1/28* | (2006.01) | |
| *A61B 90/70* | (2016.01) | |
| *B08B 9/043* | (2006.01) | |
| *B08B 3/08* | (2006.01) | |
| *A61B 6/00* | (2006.01) | |
| *B05C 1/06* | (2006.01) | |
| *A61M 25/00* | (2006.01) | |

(52) U.S. Cl.
CPC .............. *A61B 90/70* (2016.02); *B05D 1/28* (2013.01); *B08B 9/0436* (2013.01); *A61B 6/481* (2013.01); *A61M 2025/0062* (2013.01); *B05C 1/06* (2013.01); *B08B 3/08* (2013.01)

(58) Field of Classification Search
CPC ...... B05D 1/28; B08B 9/023; D06M 2400/00; B05C 1/06
See application file for complete search history.

(56) References Cited

U.S. PATENT DOCUMENTS 221,981 A * 11/1879 Taylor ...................... B05C 1/06
118/208
1,668,385 A 5/1928 Szekely et al.
(Continued)

FOREIGN PATENT DOCUMENTS

CN 202779255 U 3/2013
CN 206168831 U 5/2017
(Continued)

*Primary Examiner* — Nathan H Empie
(74) *Attorney, Agent, or Firm* — Stephen E. Kelly; Hill Ward Henderson, P.A.

(57) ABSTRACT

A method of guiding an angiographic wire while delivering fluid solvent to the wire. The method incorporates a guide device comprising a housing that is mated to a base in a manner that defines an aperture for slidably receiving the angiographic wire. A plunger is disposed within the housing in a vertically adjustable manner such that the plunger has an open position, a closed position, and one or more intermediate positions relative to the housing. The angiographic wire is placed in the aperture, and the housing is mated to the base such that the wire is slidably retained in the aperture. The plunger is depressed such that a compression pad on the plunger is placed in contact with the wire, the wire being slidably retained between the compression pad and a base pad attached to the base.

20 Claims, 4 Drawing Sheets

(56) References Cited

U.S. PATENT DOCUMENTS

| | | | |
|---|---|---|---|
| 1,748,900 A | 2/1930 | Pilla | |
| 2,222,191 A | 11/1940 | Zisman | |
| 3,098,373 A | 7/1963 | Langston | |
| 3,951,235 A * | 4/1976 | Acerbi | F16N 11/06 |
| | | | 184/46 |
| 4,038,546 A * | 7/1977 | Jasinski | G03G 15/0258 |
| | | | 361/229 |
| 4,601,918 A | 7/1986 | Zaman et al. | |
| 4,749,059 A * | 6/1988 | Jonnes | F16N 7/12 |
| | | | 118/DIG. 18 |
| 5,022,493 A | 6/1991 | Buckelew | |
| 5,070,569 A | 12/1991 | Wilkins | |
| 5,107,961 A | 4/1992 | Schott et al. | |
| 5,242,428 A | 9/1993 | Palestrant | |
| 5,334,166 A | 8/1994 | Palestrant | |
| 5,985,028 A | 11/1999 | Cornell et al. | |
| 6,554,808 B1 | 4/2003 | Cook | |
| 6,558,060 B1 | 5/2003 | Raju | |
| 6,783,593 B2 | 8/2004 | Selcer et al. | |
| 7,143,866 B2 | 12/2006 | Coder et al. | |
| 7,335,053 B2 | 2/2008 | Avevor et al. | |
| 7,900,892 B2 | 3/2011 | Student et al. | |
| 9,108,027 B2 | 8/2015 | Eubanks et al. | |
| 9,127,786 B1 | 9/2015 | Arratia | |
| 9,334,947 B2 | 5/2016 | Varghese et al. | |
| 9,499,318 B2 | 11/2016 | Mohika | |
| 2009/0304410 A1 * | 12/2009 | Tanaka | G03G 15/0258 |
| | | | 399/100 |
| 2010/0006738 A1 | 1/2010 | Teirstein | |
| 2010/0010475 A1 | 1/2010 | Teirstein et al. | |
| 2012/0216385 A1 | 8/2012 | Taylor | |
| 2015/0174619 A1 | 6/2015 | Clements | |

FOREIGN PATENT DOCUMENTS

| | | |
|---|---|---|
| SU | 1660787 A1 | 7/1991 |
| WO | WO 2010031581 A1 | 3/2010 |

* cited by examiner

METHOD FOR CLEANING AND LUBRICATING AN ANGIOGRAPHIC WIRE WITH FLUID SOLVENT DELIVERY

CROSS-REFERENCE TO RELATED APPLICATION

Pursuant to 35 U.S.C. § 120, this application is a divisional of U.S. patent application Ser. No. 16/016,202 filed on Jun. 22, 2018, the entire contents of which are incorporated herein by this reference.

BACKGROUND

1. Field of Invention

The present invention relates generally to the field of angiographic wire management, and more particularly, to an angiographic wire guide device capable of delivering fluid solvent to the surface of the wire.

2. Description of Related Art

Angiographic procedures involve inserting a tube, wire, or catheter into the human body. Prior to insertion, these long, flexible members must be sterilized to avoid infection in the patient, and they must be lubricated to promote ease of insertion into and removal from the patient's body. Each time a wire is removed from a patient, the wire must be cleaned of bodily fluids and coiled or stored in a manner that enables sterile handling.

Since these tubes, wires, or catheters are long and flexible, they are difficult to handle and maneuver, and they can easily become contaminated through careless handling or inadvertent contact with unsanitary objects. In many instances, the user must use one or both hands to attend to the patient, meaning that the wire or tubes are frequently left unattended at least for some time during the angiographic procedure. This increases the risk of entanglement or contamination of the wire.

The present guide device seeks to overcome these problems by providing a guide device capable of delivering fluid solvent to an angiographic wire or catheter while being easy to operate and manipulate.

SUMMARY OF THE PREFERRED EMBODIMENTS

The angiographic wire guide device comprises a housing and a base that mate together to define one or more apertures to receive the angiographic wires, and a plunger disposed inside the housing.

The base comprises a cradle for receiving a base pad. In one embodiment of the base, the cradle has four sidewalls, and two of the opposing sidewalls comprise a recess. The base pad is a padded member having absorbent properties capable of retaining fluid solvents.

The housing and the base are releasably connected to each other by a connection mechanism configured for releasably securing the housing in a closed position with respect to the base. In this closed position, the arched portion in the housing and the recess in the sidewalls in the base mate together to define the aperture extending through the guide device.

The plunger is disposed inside the housing in a vertically adjustable manner. In one embodiment, the plunger has a piston attached to a compression pad, which has the same absorbent properties as that of the base pad.

The guide device further comprises a locking mechanism configured to releasably retain the plunger in fixed relation to the housing. The plunger can thus be disposed in an open position, a closed position, or one or more intermediate positions with respect to the housing.

In one embodiment, the guide device further comprises one or more ports for receiving fluid solvents for cleaning and lubricating the angiographic wires. For example, in one embodiment, a port disposed in the base is placed in fluid communication with the base pad via a channel. The fluid received via the port flows through the channel to the cradle, where the fluid impregnates the base pads. The fluid in the base pad is then emitted from the base pad as the angiographic wire exerts pressure on the base pad, thereby coating the angiographic wire in the fluid solvent and cleaning and lubricating the angiographic wires.

DETAILED DESCRIPTION OF THE PREFERRED EMBODIMENTS

With reference to the drawings, the guide device will now be described with regard for the best mode and the preferred embodiments. In general, the device disclosed herein is a guide device for slidably retaining angiographic wires during an angiographic procedure. The embodiments disclosed herein are meant for illustration and not limitation of the inventive scope. An ordinary practitioner will appreciate that it is possible to create many variations of the following embodiments without undue experimentation, and that the present guide device is suitable for use with other wires and tubes intended for insertion into the human body. Examples include catheters and sheaths. For the purposes of illustration, the following discussion is presented in terms of an angiographic wire.

Figure 1:
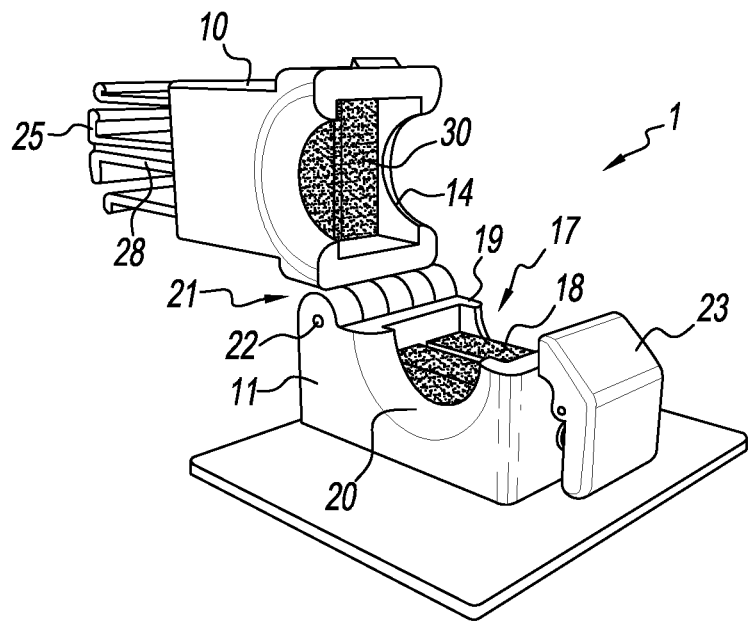
FIG. 1 is a perspective view of one embodiment of the angiographic wire guide device with the connection mechanism disengaged and the housing rotatably removed from the base.
Figure 2:
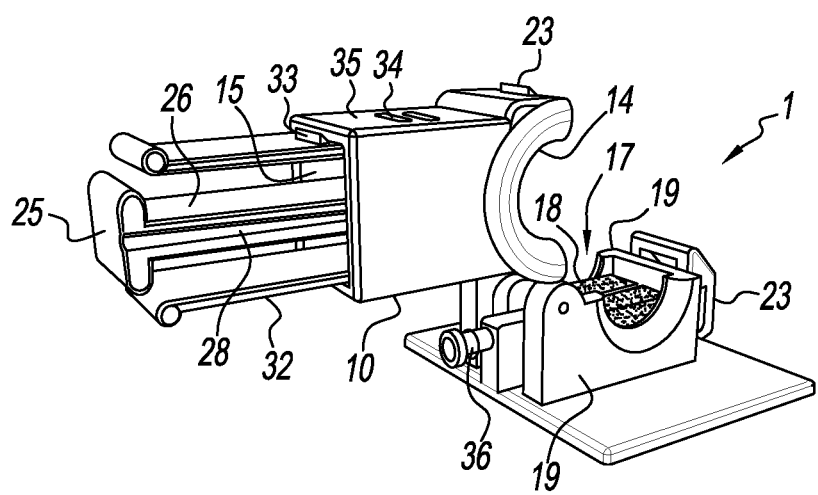
FIG. 2 is a perspective view of one embodiment of the angiographic wire guide device with the connection mechanism disengaged and the housing rotatably removed from the base.
Figure 3:
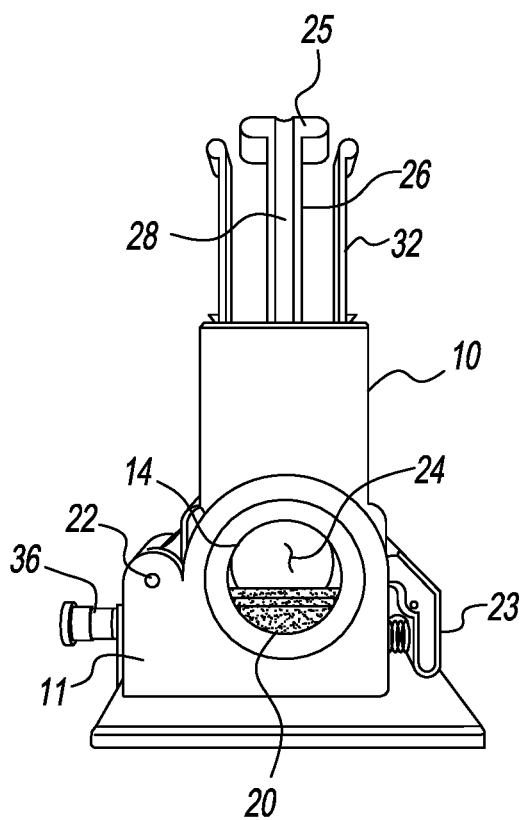
FIG. 3 is front view of one embodiment of the angiographic wire guide device with the connection mechanism fully engaged and the plunger disposed in the open position.

Referring to FIGS. 1-3, in one embodiment, the angiographic wire guide device 1 comprises a housing 10 and a base 11 that mate together to define one or more apertures 24 to receive the angiographic wires 5, and a plunger 25 disposed inside the housing 10. The housing 10 has an elongated hollow portion that is generally rectangular in cross section. Other cross-sectional shapes, such as circular, triangular, square, or the like, can be used without undue experimentation. The housing 10 further comprises an arched portion 14. In one embodiment, the inside surface 15 of the housing 10 further comprises one or more guide members, such as a ridge, knob, detent, or other protrusion.

The base 11 comprises a cradle 17 for receiving a base pad 18. In one embodiment of the base 11, the cradle 17 has four sidewalls 19, and two of the opposing sidewalls 19 comprise a recess 20 with a circular shape, an arced shape, or some other suitable shape. The base pad 18 is a padded member having absorbent properties capable of retaining fluid solvents, and then emitting such fluid solvents when the base pad 18 is placed under pressure. The material of the base pad 18 may be any suitable absorbent material, such as sponge or sponge-like material, absorbent foam, woven or non-woven fabric, paper based material, absorbent synthetic material, or the like.

With continued reference to FIGS. 1-3, the housing 10 and the base 11 are releasably connected to each other by a connection mechanism 21. Suitable connection mechanisms 21 include a variety of latches, clasps, hooks, quick-connects, and similar mechanisms. For example, one embodiment of the connection mechanism 21 comprises a hinge 22 disposed as a connection between the housing 10 and the base 11, and a clasp mechanism 23 located on the opposite side of the housing 10 and base 11 for releasably securing the housing 10 in a closed position with respect to the base 11. In this closed position (shown in FIG. 3), the arched portion 14 in the housing 10 and the recess 20 in the sidewalls 19 in the base 11 mate together to define an aperture 24 extending through the guide device 1. The aperture 24 is sized to receive angiographic wires 5 of a variety of sizes and shapes.

The plunger 25 is snugly disposed inside the housing 10 in a vertically adjustable manner. In one embodiment, shown in FIG. 4, the plunger 25 comprises a shaft 26 and a piston 27. The shaft 26 may comprise a groove 28 for slidably receiving the guide member. The shaft 26 is disposed in the housing 10 such that the guide member protrudes into the groove 28, thereby guiding the vertical adjustability of the plunger 25 in relation to the housing 10. It is preferable, but not required, that the groove 28 comprises a stop 29 disposed such to prevent the plunger 25 from travelling too far in relation to the housing 10. For example, the stop 29 could be positioned at the bottom of the groove 28 to prevent the plunger 25 from exiting the top portion of the housing 10.

Referring again to FIG. 1, in one embodiment of the plunger 25, the piston 27 further comprises a compression pad 30, the compression pad 30 being a padded member having absorbent properties similar to that of the base pad 18. It is preferable, but not required, that the compression pad 30 is made of the same material as that of the base pad 18.

Referring to FIGS. 1-3, the guide device 1 further comprises a locking mechanism 31 configured to releasably retain the plunger 25 in fixed relation to the housing 10. In one embodiment, the locking mechanism 31 comprises a locking arm 32 operably attached to the plunger 25, a locking tab 33 attached to the locking arm 32, and one or more slots 34 disposed in a sidewall 35 of the housing 10. The operable connection between the locking arm 32 and the plunger 25 could be either a direct connection or an indirect connection, such as by a spacer or other suitable linking member. In this embodiment, the locking mechanism 31 is activated when the plunger 25 is vertically adjusted with respect to the housing 10 such that the locking tab 33 becomes aligned with a slot 34. The locking tab 33 then protrudes into the slot 34, thereby retaining the plunger 25 in fixed relation to the housing 10. The locking mechanism 31 is released by forcing the locking arm 32 toward the shaft 26 of the plunger 25, thereby causing the locking tab 33 to be retracted from the slot 34. Once the locking tab 33 becomes free and clear from the slot 34, the plunger 25 is once again free to be vertically adjusted in relation to the housing 10.

Figure 5:
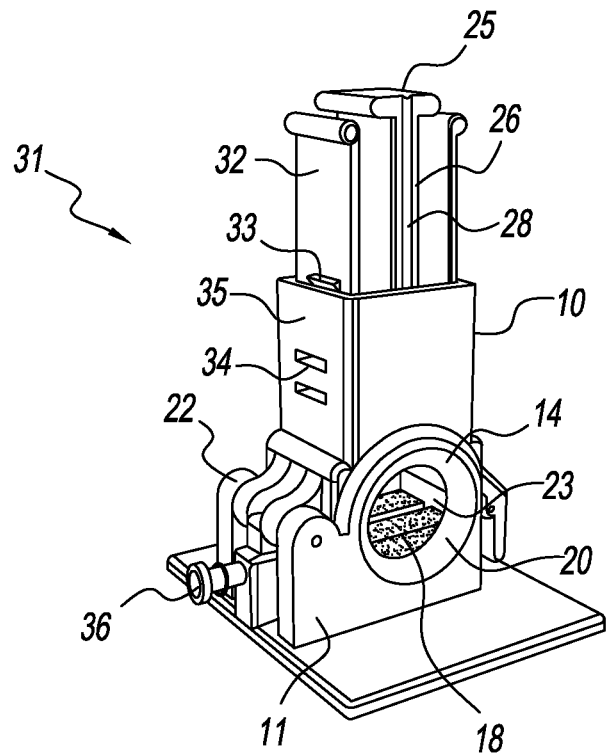
FIG. 5 is a perspective view of one embodiment of the guide device with the plunger disposed in an open position.
Figure 6:
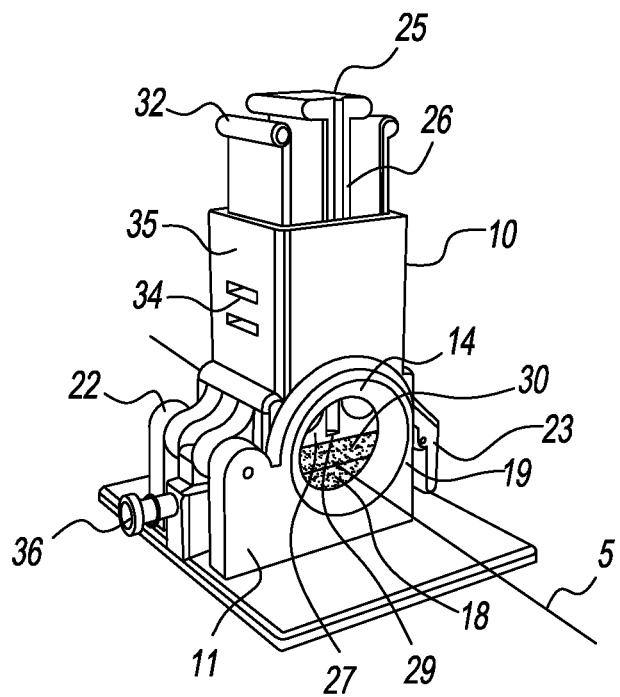
FIG. 6 is a perspective view of one embodiment of the guide device with the plunger disposed in an intermediate position.
Figure 7:
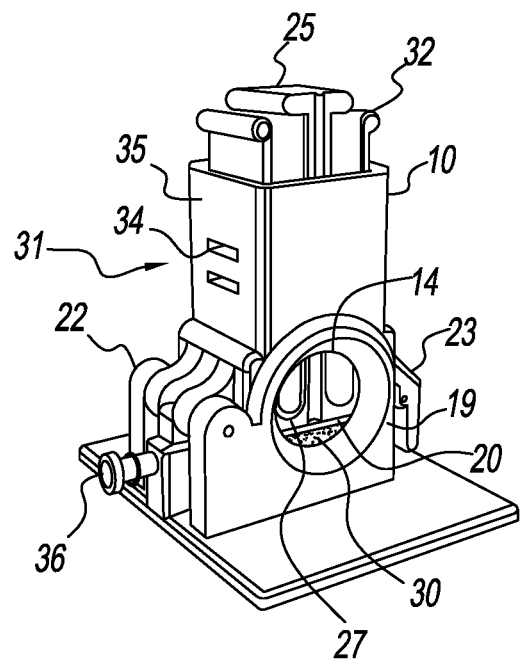
FIG. 7 is a perspective view of one embodiment of the guide device with the plunger disposed in a closed position.

Referring to FIGS. 5-7, it is preferable, but not required, that the housing 10 comprise a plurality of slots 34 such that the plunger 25 can be locked in a variety of positions with respect to the housing 10. For example, in an embodiment where the housing 10 comprises two slots 34 in a sidewall 35, the plunger 25 has an open position, one or more intermediate positions, and a closed position. The open position occurs when the locking tab 33 is located above the top slot 34 so that the locking mechanism 31 is not engaged. The intermediate position occurs when the plunger 25 is lowered such that the locking tab 33 enters the top slot 34, thus resulting in the plunger 25 being releasably locked in the intermediate position. The closed position occurs when the plunger 25 is disposed such that the locking tab 33 is within the bottom slot 34. It is preferable, but not required, that in the closed position the compression pad 30 is placed in contact with the base pad 18.

In a variation of the foregoing embodiment of the locking mechanism 31, the locking tab 31 could be placed on the inside surface 15 of the housing 10, and the one or more slots 34 could be disposed on the locking arm 32. This orientation of the locking tab 33 and the slot 34 is equivalent to the embodiment of the locking mechanism 31 described above. Notably, the locking mechanism 31 can have many slots 34 for receiving a locking tab 33, which enables the plunger 25 to be releasably locked in many different positions. This is advantageous when the guide device 1 is intended to be used with a wide variety of wire or tube-like members, such as catheters, wires, hoses, conduits, or the like.

Figure 4:
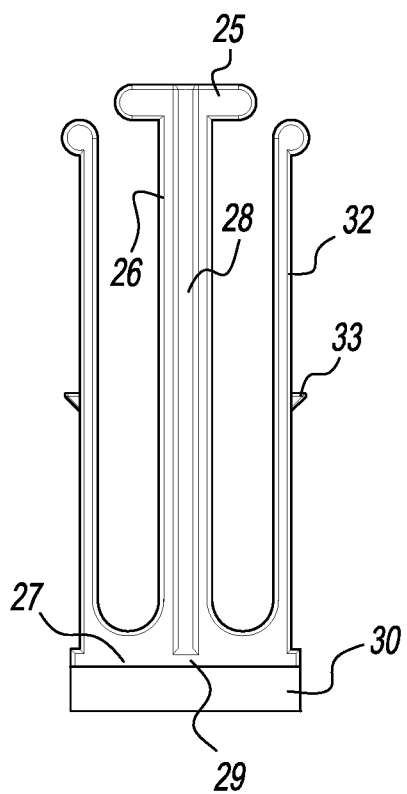
FIG. 4 is a front view of one embodiment of a plunger in the guide device.

In any of the foregoing embodiments of the locking tabs 33, the locking tabs 33 can be beveled to promote the ease of one-way movement (see FIG. 4). In this configuration, it is preferred, but not required, that the bevel is oriented such that the plunger 25 can be depressed toward the base 11 with ease, and automatically seat into the slot 34. This enables one-handed manipulation of the guide device 1 by the user, thereby freeing the other hand of the user to attend to the patient undergoing the angiographic procedure.

Figure 8:
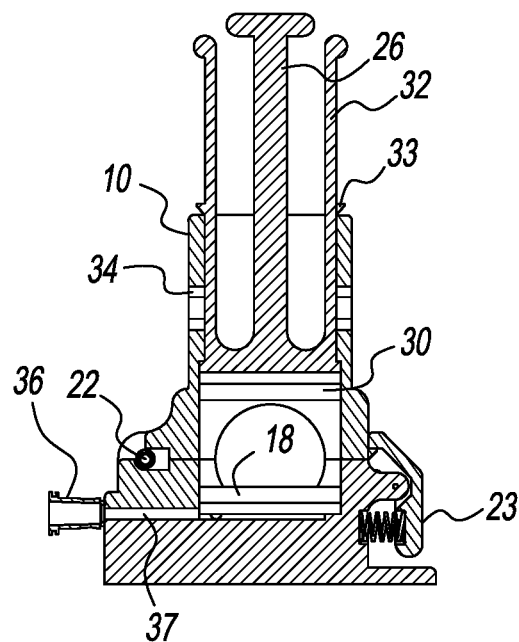
FIG. 8 is a cross section of one embodiment of the base, showing the fluid communication between the port and the cradle of the base.

In one embodiment of the guide device 1, the guide device 1 further comprises one or more ports 36 for receiving fluid solvents for cleaning and lubricating the angiographic wires 5. The one or more ports 36 could be disposed on the housing 10, the base 11, or both. Each port 36 receives the fluid solvents by any known method, such as from a feed tube or syringe. The housing 10 or the base 11, as the case may be, comprises a channel 37 (see FIG. 8) disposed in fluid communication with the compression pad 30 or the base pad 18. For example, referring to FIG. 8, a port 36 disposed in the base 11 is placed in fluid communication with the base pad 18 via channel 37. The fluid received via the port 36 flows through the channel 37 to the cradle 17, where the fluid impregnates the base pads 18. The fluid in the base pad 18 is then emitted from the base pad 18 as the angiographic wire 5 exerts pressure on the base pad 18, thereby coating the angiographic wire 5 in the fluid solvent and cleaning and lubricating the angiographic wires 5 during the procedure.

In use, the guide device 1 is placed on a suitable surface with the base 11 down, the connection mechanism 21 open, and the plunger 25 placed in the open position. The angiographic wire 5 is seated in the recess 20 in the base 11, which causes the angiographic wire 5 to be placed in contact with the base pad 18 resting in the cradle 17. The connection mechanism 21 is then engaged such that the housing 10 is mated to the base 11 such that the angiographic wire 5 is slidably disposed in the aperture 24. With the plunger 25 placed in this open position, the aperture 24 acts as a guide for slidably maneuvering the angiographic wire 5 as desired.

The plunger 25 is then depressed until the compression pad 30 is placed in contact with the angiographic wire 5. In this position, only light pressure is exerted on the angiographic wire 5 by the compression pad 30 and the base pad 18. Thus, the angiographic wire 5 can be slid back and forth through the aperture 24, thereby causing the angiographic wire 5 to be coated in fluid solvent. To retain the angiographic wire 5 in a fixed position, the plunger 25 is further depressed until the locking mechanism 31 reaches the closed position of the plunger 25. In this position, the pressure exerted on the angiographic wire 5 by the compression pad 30 and the base pad 18 causes a friction force between the pads 30, 18 and the wire 5 so that the angiographic wire 5 is more firmly retained in place.

In another embodiment of the guide device 1, which further demonstrates the foregoing friction levels, the angiographic wire 5 is inserted into the aperture 24 and the plunger 25 is depressed until the locking mechanism 31 reaches a first intermediate position with the compression pad 30 placed in contact with the angiographic wire 5. This arrangement produces a first level of friction between the angiographic wire 5 and the compression pad 30. The plunger 25 can then be further depressed until the locking mechanism 31 reaches a second intermediate position, which produces a second level of friction between the angiographic wire 5 and the compression pad 30, the second level of friction having a friction magnitude higher than that of the first level of friction. The plunger 25 can then be further depressed until the locking mechanism 31 reaches a third intermediate position, which produces a third level of friction between the angiographic wire 5 and the compression pad 30, the third level of friction having a friction magnitude higher than that of the second level of friction. This process can continue for any desired number of intermediate positions until the locking mechanism 31 reaches the closed position.

In use, the guide device 1 can be attached to a surgical drape or other sterile surface within a surgical field. This attachment is accomplished by one or more attachment mechanisms, such as adhesives, high friction pads, hook and loop closures, clips, or the like. One embodiment of the guide device 1 has a weighted base to assist with the attachment mechanism. For example, the weighted base may be of particular use when the attachment mechanism includes adhesives, high friction pads, hook and loop material, or other mechanisms that would be assisted by the weighted base. Additionally, multiple guide devices 1 can be used in series to secure a single wire or tube, or in parallel to secure multiple wires or tubes.

The foregoing embodiments are merely representative of the angiographic wire guide device and not meant for limitation of the invention. For example, persons skilled in the art would readily appreciate that there are several embodiments and configurations of locking mechanisms, connection mechanisms, and other components will not substantially alter the nature of the guide device. Likewise, elements and features of the disclosed embodiments could be substituted or interchanged with elements and features of other embodiments, as will be appreciated by an ordinary practitioner. Consequently, it is understood that equivalents and substitutions for certain elements and components set forth above are part of the invention described herein, and the true scope of the invention is set forth in the claims below.

We claim:

1. A method of cleaning and lubricating a wire or tube intended for insertion into a patient's body, the method comprising the steps of:
   providing a guide device comprising:
      a housing and a base, the housing mated to the base to define an aperture, the base comprising a base pad;
      a plunger disposed within the housing in a vertically adjustable manner such that the plunger has an open position, a closed position, and one or more intermediate positions relative to the housing, the plunger comprising a compression pad disposed such that the compression pad abuts the base pad when the plunger is disposed in the closed position;
      a locking mechanism configured to releasably lock the plunger in the closed position or the one or more intermediate positions, the locking mechanism comprising: a flexible locking arm operably connected to the plunger, the locking arm having a locking tab disposed on the locking arm; and a plurality of slots disposed in the housing, the slots configured for removably receiving the locking tab; and
      a port fluidly connected to the compression pad and the base pad, the compression pad and the base pad configured for absorbing lubricating fluid;
   placing the wire or tube in contact with the base pad;
   mating the housing to the base such that the wire or tube is slidably retained in the aperture; and
   depressing the plunger such that the compression pad is placed in contact with the wire or tube, the wire or tube being slidably retained between compression pad and the base pad.

2. The method of claim 1, further comprising the step of activating the locking mechanism such that the plunger is retained in an intermediate position.

3. The method of claim 1, further comprising the steps of:
   introducing lubricating fluid into the port; and
   dispensing the lubricating fluid onto the wire or tube via the compression pad or the base pad.

4. The method of claim 2, further comprising the steps of:
   introducing lubricating fluid into the port; and
   dispensing the lubricating fluid onto the wire or tube via the compression pad or the base pad.

5. The method of claim 1, further comprising the steps of:
   introducing sterilization fluid into the port; and
   dispensing the sterilization fluid onto the wire or tube via the compression pad or the base pad.

6. The method of claim 2, further comprising the steps of:
   introducing sterilization fluid into the port; and
   dispensing the sterilization fluid onto the wire or tube via the compression pad or the base pad.

7. The method of claim 1, further comprising the step of providing one or more additional guide devices in series to secure the wire or tube.

8. The method of claim 1, further comprising the steps of attaching the base of the guide device to a surgical drape.

9. The method of claim 5, further comprising the steps of providing one or more additional guide devices in series to secure the wire or tube.

10. The method of claim 9, further comprising the steps of attaching the base of each guide device to a surgical drape.

11. A method of cleaning and lubricating a wire or tube intended for insertion into a patient's body, the method comprising the steps of:
    providing a guide device comprising:
        a housing and a base, the housing mated to the base to define an aperture, the base comprising a base pad;
        a plunger disposed within the housing in a vertically adjustable manner such that the plunger has an open position, a closed position, and one or more intermediate positions relative to the housing, the plunger comprising a compression pad disposed such that the compression pad abuts the base pad when the plunger is disposed in the closed position;
        a locking mechanism configured to releasably lock the plunger in the closed position or the one or more intermediate positions, the locking mechanism comprising: a flexible locking arm operably connected to the plunger, the locking arm having a locking tab disposed on the locking arm; and a plurality of slots disposed in the housing, the slots configured for removably receiving the locking tab; and
        a port fluidly connected to the compression pad and the base pad, the compression pad and the base pad configured for absorbing lubricating fluid;
    placing the wire or tube in contact with the base pad;
    mating the housing to the base such that the wire or tube is slidably retained in the aperture;
    depressing the plunger such that the locking mechanism reaches a first intermediate position with the compression pad placed in contact with the wire or tube, thereby producing a first level of friction between the compression pad and the wire or tube; and
    depressing the plunger such that the locking mechanism reaches a second intermediate position, thereby producing a second level of friction between the compression pad and the wire or tube, the second level of friction having a magnitude higher than that of the first level of friction.

12. The method of claim 11, further comprising the steps of:
    introducing sterilization fluid into the port; and
    dispensing the sterilization fluid onto the wire or tube via the compression pad or the base pad.

13. The method of claim 11, further comprising the step of providing one or more additional guide devices in series to secure the wire or tube.

14. The method of claim 11, further comprising the step of attaching the base of the guide device to a surgical drape.

15. The method of claim 13, further comprising the step of attaching the base of each guide device to a surgical drape.

16. The method of claim 11, further comprising the step of depressing the plunger such that the locking mechanism reaches a third intermediate position, thereby producing a third level of friction between the compression pad and the wire or tube, the third level of friction having a magnitude higher than that of the second level of friction.

17. The method of claim 16, further comprising the steps of:
    introducing sterilization fluid into the port; and
    dispensing the sterilization fluid onto the wire or tube via the compression pad or the base pad.

18. The method of claim 16, further comprising the step of providing one or more additional guide devices in series to secure the wire or tube.

19. The method of claim 16, further comprising the step of attaching the base of the guide device to a surgical drape.

20. The method of claim 18, further comprising the step of attaching the base of each guide device to a surgical drape.

\* \* \* \* \*